(12) United States Patent
Haddad et al.

(10) Patent No.: US 9,464,171 B2
(45) Date of Patent: Oct. 11, 2016

(54) PERIPHERALLY AROMATIC SILSESQUIOXANES FEATURING REACTIVE FUNCTIONALITY: SYNTHESIS AND APPLICATION THEREOF

(71) Applicant: The United States of America as Represented by the Secretary of the Air Force, Washington, DC (US)

(72) Inventors: Timothy S. Haddad, Lancaster, CA (US); Joseph M. Mabry, Lancaster, CA (US); Gregory R. Yandek, Tehachiapi, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/611,319

(22) Filed: Feb. 2, 2015

(65) Prior Publication Data

US 2015/0148497 A1    May 28, 2015

Related U.S. Application Data

(62) Division of application No. 13/210,915, filed on Aug. 16, 2011, now Pat. No. 8,981,140.

(60) Provisional application No. 61/374,669, filed on Aug. 18, 2010.

(51) Int. Cl.

| | |
|---|---|
| *C07F 7/21* | (2006.01) |
| *C08G 73/10* | (2006.01) |
| *C07F 7/00* | (2006.01) |
| *C08G 59/14* | (2006.01) |
| *C08G 69/48* | (2006.01) |
| *C08G 71/02* | (2006.01) |
| *C08G 73/06* | (2006.01) |
| *C07F 7/08* | (2006.01) |
| *C08G 77/04* | (2006.01) |

(52) U.S. Cl.
CPC ............. *C08G 73/1082* (2013.01); *C07F 7/00* (2013.01); *C07F 7/087* (2013.01); *C07F 7/0843* (2013.01); *C07F 7/0874* (2013.01); *C07F 7/21* (2013.01); *C08G 59/1477* (2013.01); *C08G 69/48* (2013.01); *C08G 71/02* (2013.01); *C08G 73/06* (2013.01); *C08G 77/04* (2013.01)

(58) Field of Classification Search
CPC ................................. C07F 7/0874; C07F 7/21
See application file for complete search history.

(56) References Cited

U.S. PATENT DOCUMENTS

| | | | |
|---|---|---|---|
| 8,981,140 B1 * | 3/2015 | Haddad | C07F 7/21 556/455 |
| 2006/0194068 A1 * | 8/2006 | Katoh | C08G 73/106 428/447 |

* cited by examiner

*Primary Examiner* — Sudhakar Katakam
(74) *Attorney, Agent, or Firm* — AFMCLO/JAZ; Chastity Whitaker

(57) ABSTRACT

Methods of synthesis and application thereof for peripherally aromatic silsesquioxanes featuring reactive functionality. A method, according to one embodiment of the invention, includes reacting a polyhedral oligomeric silsesquioxane with an anhydride. The polyhedral oligomeric silsesquioxane has an inorganic core, a phenyl moiety or an anlyine moiety covalently coupled to the at least one T-type silicon atom; and a metal-aniline group or a para-aniline group covalently coupled to the at least one D-type or M-type silicon atom. The inorganic core includes 6-14 silicon atoms, at least one of the silicon atoms being an M-type silicon atom or a D-type silicon atom, and at least one of the silicon atoms being a T-type silicon atom, and 9-20 oxygen atoms.

14 Claims, 5 Drawing Sheets

PERIPHERALLY AROMATIC SILSESQUIOXANES FEATURING REACTIVE FUNCTIONALITY: SYNTHESIS AND APPLICATION THEREOF

Pursuant to 37 C.F.R. §1.78(c)(3), this application is a divisional application, claiming the benefit of and priority to prior filed co-pending application Ser. No. 13/210,915, filed Aug. 16, 2011, which claims the benefit and priority to prior filed Provisional Application Ser. No. 61/374,669, filed Aug. 18, 2010. The disclosures of these applications are expressly incorporated herein by reference, in their entireties.

RIGHTS OF THE GOVERNMENT

The invention described herein may be manufactured and used by or for the Government of the United States for all governmental purposes without the payment of any royalty.

FIELD OF THE INVENTION

This invention relates to synthesis methods and applications for the production and use of organic/inorganic hybrid polyhedral oligomeric silsesquioxane (POSS) nanomaterials.

BACKGROUND OF THE INVENTION

The dispersion of nanoscopic particles in host polymers has resulted in well-documented improvements in various properties such as thermo-oxidative stability, response to mechanical load, thermal expansion, space survivability, abrasion resistance, moisture uptake, electrical characteristics, and other surface-related properties. As a result, the application of nanotechnology has enabled an expansion in the end-use envelope of many organic materials. Nanoparticles classified as polyhedral oligomeric silsesquioxanes, or POSS, have proven to be a particularly effective class of additives due to their inherent size, shape, rigidity, and versatility in function. The ability to chemically tailor POSS through synthetic manipulation over its organic periphery offers a unique design tool for controlling particle affinity and resultant dispersion in host materials. The number of peripheral substituents is dependent on the size of the silsesquioxane cage itself, or more precisely, the number of silicon atoms contained within the cage. The nature of those substituents may be depends on the limitations defined by state-of-the-art POSS synthesis methods. There are advantages and disadvantages in the choice of an inert or reactive periphery. In general, inert functionalities do not require an adjustment of polymerization stoichiometry or impose complications arising from differences in the reaction kinetics amongst the involved chemical species; however, inert functionalities provide limited control in the formation of desired material morphologies and increased possibility for nanoparticle flux to a more desired energy state over time that may result in a possible degradation of properties during such a process. Reactive moieties, on the other hand, allow for more precise control over copolymer architecture and impede nanoparticle migration over time (due to covalent attachment to host); however, reactive moieties, require stoichiometric balance that is often hindered by steric restraints. A review of the current state of inert and reactive POSS technologies may be found in FINA, A. et al., *Journal of Materials Chemistry* 2010, 20(42), 9297-9305. Overall, selection of the POSS periphery should be based on the structure of the polymer that is intended to be modified and the desired end-use properties.

To date, an array of POSS molecules have been developed for a variety of applications. While POSS is useful as a commercial additive, there are currently some limitations in its utility. The limitations are especially true in the modification of high temperature polymers, due to a general weakness in the thermal stability of organic peripheries with C—C bonds having dissociation energies in the close proximity of 80 kcal/mol. Currently, the most thermally robust versions of POSS have cages functionalized with complete inert aromaticity. Examples include Octaphenyl™ and Dodecaphenyl™ POSS, which feature pure phenyl moieties comprised of C=C bonds having dissociation energies of approximately 150 kcal/mol. Unfortunately, such molecules demonstrate a propensity to crystallize to the extent that their assembled aggregation is unaffected by shear forces imposed by conventional polymer blending and compounding methods. Crystallization is also to the extent that the exemplary POSS cages degrade during the melting process, both characteristics preventing effective dispersion into host materials. From a structural perspective, POSS molecules readily crystallize due to the rigid and regular nature of the silsesquioxane cage itself. This propensity for crystallization has been shown to be disrupted through the design and synthesis of a heterogeneous organic periphery, which is described in MOORE et al., *Journal of Organometallic Chemistry* 2011, 696(13), 2676-2680. The achievement of a balance between good thermal stability and dispersability lies in molecular design.

To maximize the full benefits of POSS incorporation into polymer hosts, such as in terms of the delivered composite properties, the POSS molecules design requires consideration of molecular assembly during incorporation into a polymer host. For POSS molecules possessing a reactive or partially reactive periphery, geometric forethought of the attachment route with a polymer host network is necessary. For example, POSS may be incorporated through copolymerization by strategic placement of the silsesquioxane cage in the main chain ("bead-on-a-string") of a growing polymer chain or network, as described in U.S. Pat. No. 6,767,930, issued to SVEJDA et al., or conversely, in a pendant, or dangling-type conformation, such as is described in WRIGHT et al., *Macromolecules* 2006, 39(14), 4710-4718. The resulting architectures often yield a marked difference in morphology and as a result, in delivered properties.

In terms of imparting reactive functionality to POSS, amine groups offer the most versatility due to their compatibility with many types of polymers, viz. epoxies, cyanate esters, and polyimides (both thermoplastic and thermosetting in nature). Twelve varieties of amino-containing POSS molecules are commercially-available, however, all but one of those compounds contain peripheries comprised of thermally labile chemical groups, i.e., any combinations of isobutyl, isooctyl, cyclohexyl, ammonium, aminoethyl, and aminopropyl groups. POSS molecules have been used to modify various polymers which are the subject of various patents. In the high temperature polymer area, for example, polyimides have been modified with aminopropylisobutyl POSS in POE et al., U.S. Application Publication Nos. 2009/0069508 (2008) and 2010/0063244 (2009). These types of moieties, in general, pose a thermal and solubility mismatch with polymers considered to be high temperature (largely aromatic). Disassociation of the POSS organic periphery can produce free radicals that may react with any polymer in the immediate vicinity thus causing chain scission and property weakening. The sole commercial compound that possesses a thermally stable, homogeneous aniline periphery has the drawback of possessing a high density of reactive groups. When reactively is incorporated into a polymer, this characteristic generally contributes to either the formation of an over cross-linked network resulting in material embrittlement or incomplete amine conversion (due to steric barriers resulting in sites that exhibit an affinity to water, which are deleterious toward material aging manifested in thermo-mechanical properties). Therefore, there exists a significant need for the development of new thermally stabile, amino-functionalized POSS compounds with a lower concentration of reactive groups. Such molecules would be beneficial in the design and control of polymeric architectures for the purposes of maximizing delivered properties, especially at elevated temperatures. Further utility of the embodied aniline POSS compounds is readily derived from chemical reaction of their amine groups with anhydride compounds to form imide-type moieties with other types of reactive end-groups, notably phenylethynyl phthalic anhydride ("PEPA") (a cross-linkable group found on the ends of many high performance thermosetting oligomeric compounds). Cross-linking proceeds during consumption of the ethynyl group through cyclotrimerization to form a thermally and mechanically robust aromatic junction.

The nomenclature for silicon atoms was originally developed to distinguish silicon monomers and polymers. A silane (M) group consists of three organic groups and one oxygen atom bound to a central silicon atom. A siloxane (D) group consists of two organic groups and two oxygen atoms bound to the central silicon atom. When one organic group and three oxygen atoms bound to a central silicon atom, the group is referred to as a silsesquioxane (T) group. A silicate (Q) group consists of four oxygen atoms bound to the central silicon atom, which is not bound to any organic groups. The structure of each group is illustrated below. This method allows the simplified description of various structures.

SUMMARY OF THE INVENTION

The present invention describes previously unreported versions of POSS mono- and dianilines that feature completely aromatic peripheries for the purpose of matching the thermal and chemical capabilities of the POSS compound with high performance polymeric materials. Incorporation of these POSS mono- and dianilines into polymer hosts occurs through chemical reaction of amine moieties of the POSS compound with a variety of functionalities, including epoxies, anhydrides, and cyanate esters. The amine groups may also be further reacted with phenylethynyl phthalic anhydride ("PEPA") to yield POSS monomers useful as drop-in additives for high temperature thermosets, also possessing PEPA in their chemical structures. Resulting POSS-containing polymers generally exhibit improved processing and delivered properties.

According to an embodiment of the present invention, a method of synthesizing a thermosetting oligomeric imide includes reacting a polyhedral oligomeric silsesquioxane with an anhydride. The polyhedral oligomeric silsesquioxane has an inorganic core, a phenyl moiety or an anlyine moiety covalently coupled to the at least one T-type silicon atom; and a metal-aniline group or a para-aniline group covalently coupled to the at least one D-type or M-type silicon atom. The inorganic core includes 6-14 silicon atoms, at least one of the silicon atoms being an M-type silicon atom or a D-type silicon atom, and at least one of the silicon atoms being a T-type silicon atom, and 9-20 oxygen atoms. In yet other embodiments of the present invention, the polyhedral oligomeric silsesquioxane has an inorganic core, a phenyl moiety or an aniline moiety, and a meta-aniline group or a para-aniline group. The inorganic core has 6-14 silicon atoms, at least one of the silicon atoms being an M-type silicon atom or a D-type silicon atom, and at least one of the silicon atoms being a T-type silicon atom, and 9-20 oxygen atoms. The phenyl moiety or an aniline moiety is covalently coupled to the at least one T-type silicon atom. The meta-aniline group or a para-aniline group covalently coupled to the at least one D-type or M-type silicon atom. The method of synthesizing the polyhedral oligomeric silsesquioxane includes reacting the polyhedral oligomeric silsesquioxane with an anhydride.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

This invention describes syntheses and applications of novel polyhedral oligomeric silsesquioxane ("POSS") anilines and anhydride-modified derivatives thereof. The POSS compounds exhibit complete aromaticity in their heterogeneous organic peripheries. The POSS anilines may include: (1) a "bead-type" silsesquioxane diamine possessing 10 silicon atoms and 14 oxygen atoms, wherein 8 of the silicon atoms are considered T silicon atoms (covalently attached to 3 oxygen atoms) and two of the silicon atoms are D silicon atoms attached to 2 oxygen atoms with the anilines placed in the meta position relative to the attachment of the phenyl groups to the D silicon atoms; (2) heteroleptically phenyl POSS TB monoaniline isomers, where the amine group is attached in the para or meta position relative to the attachment of the phenyl group to a T silicon atom; (3) "bead-type" silsesquioxanes with the aniline groups either in the para or meta position relative to the D silicon atoms, where the amine groups are reacted with phenylethynyl phthalic anhydride ("PEPA") to form phenylethynyl phthalic imide ("PEPI") POSS molecules; and (4) the POSS TB monoaniline isomers, or any mixture thereof, reacted with PEPA to form TB mono-functional TB PEPI. Other embodiments are directed to a method of synthesizing an improved synthesis method over the state-of-the-art for an existing double-decker (T8D2) silsesquioxane diamine with the dianiline groups in the para position relative to the D silicon atoms. The uniqueness of the disclosed materials is their design for controlled incorporation into polymers that can withstand continuous service at 200-350° C. in an oxygen-rich environment (that is, high temperature polymers). In terms of chemical architecture, the POSS compounds of the present invention feature silsesquioxane cages surrounded by only phenyl and aniline moieties. POSS cages having aniline moieties are equipped for facile attachment to host systems that accept amines through chemical reaction. These reactions include, for example, polyimides through linear copolymerization and epoxies where the amines can participate in network formation through crosslinking. Complete peripheral aromaticity and a lack of thermally labile groups enable exceptional thermal stability for POSS anilines and good solubility (high optical clarity) in high temperature polymers.

Copolymerization of these types of POSS molecules with thermoplastic or thermosetting polymer systems that accept amines during chemical reaction or ethynyl groups through cyclotrimerization, viz. monomers, oligomers, or polymers having epoxide groups, anhydride groups, cyanate ester groups, or ethynyl groups, are anticipated to improve processability, short- and long-term thermo-oxidative stability, abrasion resistance, mechanical properties such as toughness, creep, coefficient of thermal expansion and tensile strength, solvent resistance, dielectric properties, and reductions in thermal expansion, moisture uptake, flammability and heat of combustion, and hydrophobicity.

Examples

1. Synthesis of Phenyl$_7$POSS Monoaniline

Synthesis of monoamine precursor, p-Cl$_3$Si[PhN(TMS)$_2$]: A solution of 4-bromo-N,N-bis(trimethylsilyl)aniline (9.48 g, 30 mmol) in 25 ml of anhydrous THF is taken in an addition funnel and slowly added to a stirring mixture of Mg (0.912 g, 38 mmol) and anhydrous THF initiated with a crystal of 12 and a drop of 4-bromo-N,N-bis(trimethylsilyl)-aniline. The reaction is allowed to stir overnight at ambient temperature, cannulated to a 250 mL round bottomed flask, and very slowly added to a stirring mixture of THF (10 mL) and silicon tetrachloride (5.35 g, 31.5 mmol). This is allowed to stir overnight. The solvent is removed, in vacuo, from the reaction mixture and dry hexane added to extract the product by filtration through celite. After removing all volatiles under a dynamic vacuum, the residual yellow colored filtrate is transferred to a 25 ml flask and distilled under dynamic vacuum to give phenyl-bis(trimethylsilyl) trichlorosilane, as a colorless, very viscous liquid in 90% yield. $^1$H NMR (CDCl$_3$) 0.136 ppm (s, 18H, NSiCH$_3$), 7.08 ppm (m, 4H), 7.73 ppm (m, 4H). $^{29}$Si NMR (CDCl$_3$) 5.81 ppm, −0.475 ppm (ratio=2:1).

Synthesis of POSS monoamine: a solution of phenyl-bis(trimethylsilyl) trichlorosilane precursor (0.89 g, 2.4 mmol), in 5 mL dry ether is added very slowly to a stirring solution of trisilanolphenyl-POSS, Ph$_7$Si$_7$O$_9$(OH)$_3$ (2.06 g, 2.2 mmol) in 10 mL dry ether and 5 mL anhydrous THF. To this is very slowly added a solution of distilled triethylamine in dry ether (0.6966 g, 6.90 mmol). This is left stirring overnight. The solution is filtered to remove NEt$_3$.HCl precipitates and rotary evaporated to slurry. The slurry is precipitated fully in 150 mL reagent grade methanol acidified with glacial acetic acid to give POSS monoamine monomer in 60% yield. $^{29}$Si NMR (CD$_2$Cl$_2$) −76.99 ppm, −78.34 ppm, −78.50 (ratio=1:4:3).

2. Synthesis of Phenyl$_7$POSS Mono-Phenylethynyl Phthalic Imide

In a 50 mL round bottom flask, a solution of PEPA (0.246 g, 1 mmol) in 35 mL toluene is added to a stirring solution of POSS phenylamine (1.05 g, 1 mmol) in 5 mL dimethylacetamide ("DMAC"). This is attached to a reverse Dean Stark apparatus which is dried in an oven, evacuated and backfilled with GN2 prior to use. The entire set up is equipped with a condenser and a thermometer. The stirring reaction mixture is heated in an oil bath at 1500° C. for 6 hr and allowed to cool to room temperature. White precipitates obtained at the bottom of the reaction flask are filtered, washed with anhydrous diethyl ether and air dried under nitrogen for 6 hr. These are further dried under vacuum at 1200° C. for 24 hr. $^{29}$Si NMR (CDCl$_3$) −78.07, −78.16, −78.67 (ratio=3:4:1).

3. Synthesis of Bis(Meta-Analine,Methyl)Silyloxy-Octaphenylsilsesquioxane ("Bead-Type") POSS Dianiline)

Under a nitrogen atmosphere, in a 50 mL round-bottomed flask phenylPOSS-tetrol, Phenyl$_8$Si$_8$O$_{10}$(OH$_4$), (2.00 g, 1.87 mmol) is suspended in 10 mL of anhydrous THF. To this stirred suspension, a solution of 3-[bis(N,N-trimethylsilyl)

phenylamino]methyl-dichlorosilane (1.376 g, 3.93 mmol) and NEt$_3$ (0.776 g, 7.67 mmol) in THF (10 mL) is slowly added in a drop-wise manner. After 30 min, the solution is filtered to remove NEt$_3$HCl (957 mg, 6.95 mmol, 93% theoretical) and the solvent is removed under vacuum. Approximately 1 mL of diethylether is added to the product followed by 20 mL of MeOH to make a well-stirred suspension of white-colored intermediate. The trimethylsilyl groups are hydrolyzed by the addition of 1 drop of concentrated acetic acid and 1 hr of stirring. The product is isolated by filtration and dried under a nitrogen stream to give a white powder in 84% yield (2.097 g, 1.57 mmol). $^1$H NMR (CDCl$_3$, δ) 7.62-6.99 ppm (m, 44H), 6.74 ppm (m, 4H), 3.3 ppm (broad s, 4H, NH$_2$), 0.58 ppm (s, 6H). $^{29}$Si NMR (CDCl$_3$) −30.5, −78.4, −79.4, −79.6, −79.8 ppm.

4. Synthesis of Bis(Aniline,Methyl)Silyloxy-Octaphenylsilsesquioxane ("Bead-Type" POSS Dianiline)

Synthesis of 4-[bis(N, N-trimethylsilyl)phenylaminio]methyldichlorosilane precursor: under a nitrogen atmosphere a solution of 4-bromo-N,N-bis(trimethylsilyl)aniline (9.48 g, 30 mmol) in 25 mL of anhydrous THF was placed in an addition funnel and slowly added to a stirring mixture of Mg (0.912 g, 38 mmol) and anhydrous THF, already initiated with a small crystal of I$_2$ and a drop of 4-bromo-N,N-bis(trimethylsilyl)aniline. The reaction was allowed to stir overnight at ambient temperature, and then slowly cannulated into a 250 mL round-bottomed flask containing a stirring mixture of THF (10 mL) and methyltri-chlorosilane (4.485 g, 30 mmol). This was allowed to stir overnight. The solvent was removed, in vacuo, from the reaction mixture and dry hexane added to extract the product by filtration through celite. After removing all volatiles under vacuum at room temperature, the remaining yellow-colored filtrate was transferred to a 25 mL flask. This was distilled at 89° C. under dynamic vacuum using a Kugelrohr apparatus to give the product as a colorless liquid in 87% yield (9.15 g, 26.1 mmol). 1H NMR (CDCl$_3$) 0.13 ppm (s, 18H, NSiCH$_3$), 1.06 ppm (s, 3H, SiCH$_3$), 7.03 ppm (m, 2H), 7.61 ppm (m, 2H). $^{29}$Si NMR (CDCl$_3$, δ) 5.2 ppm, 18.9 ppm (ratio=2:1).

Figure 1:
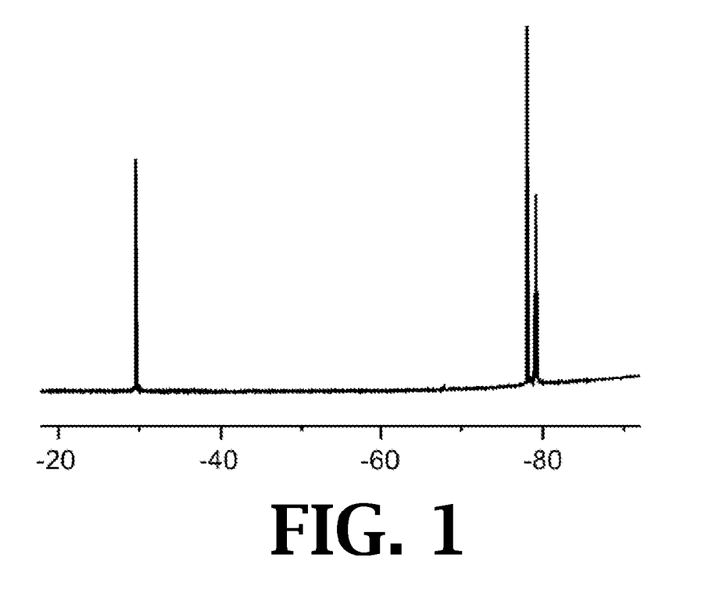
FIG. 1 is NMR spectrum of bis(para-aniline, methyl) silyloxy-octaphenylsilsesquioxane ("bead-type" POSS).
Figure 2:
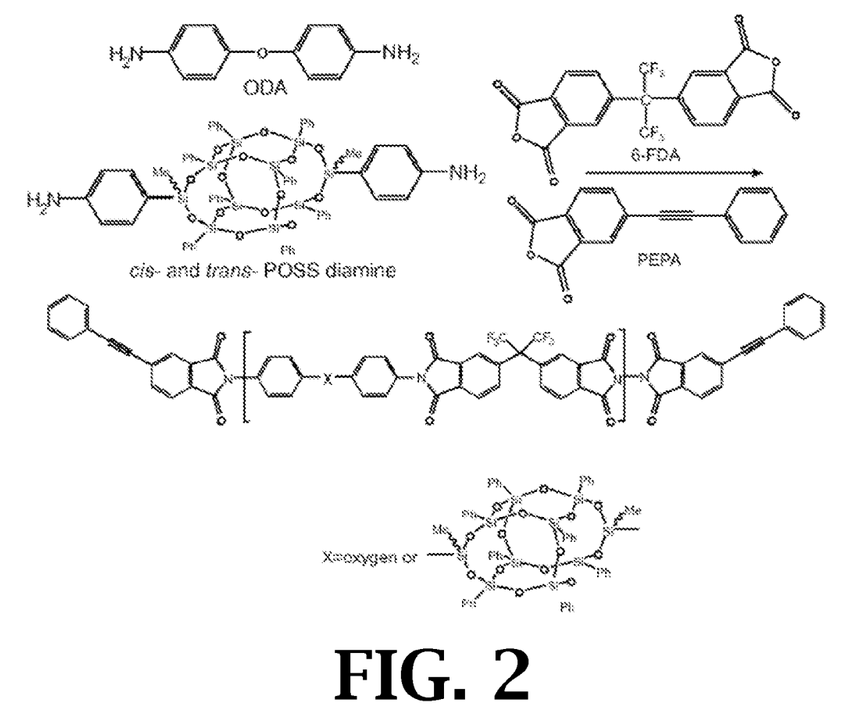
FIG. 2 is chemical structures of monomers and resultant oligoimides resulting from systematic modification of the condensation oligomer 6FDA-ODA-PEPA by substitution of ODA with "bead-type" POSS.
Figure 3A:
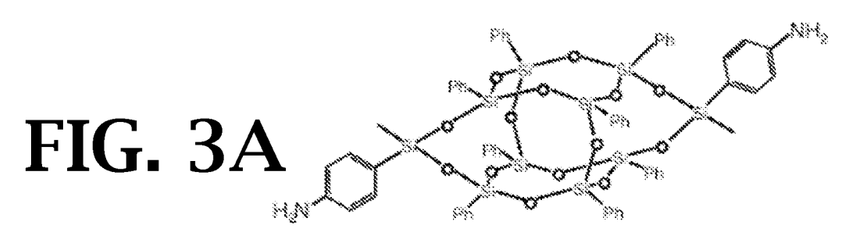
FIGS. 3A-3D exhibit representations of the chemical structures of the various conformations that "bead-type" POSS dianilines can adopt, including trans-bis(para-aniline, methyl)silyloxy-octaphenylsilsesquioxane in FIG. 3A, cis-bis(para-aniline,methyl)silyloxy-octaphenylsilsesquioxane in FIG. 3B, trans-bis(meta-aniline,methyl)silyloxy-octaphenylsilsesquioxane in FIG. 3C, and cis-bis(meta-aniline,methyl)silyloxy-octaphenylsilsesquioxane in FIG. 3D.
Figure 3B:
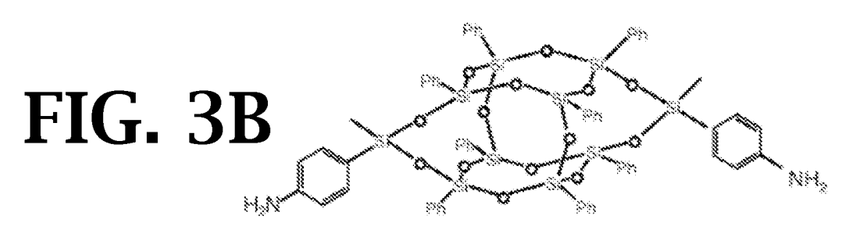
Figure 3C:
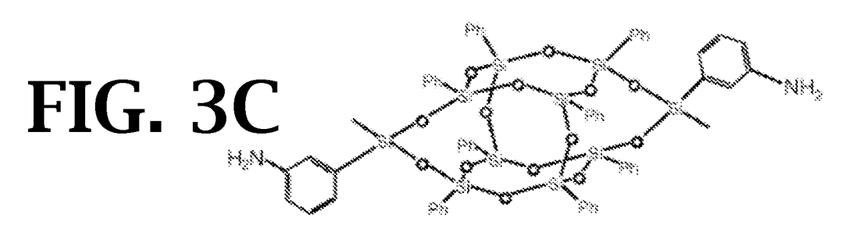
Figure 3D:
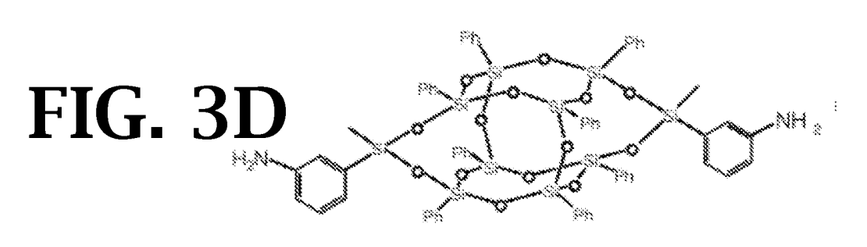
Figure 4A:
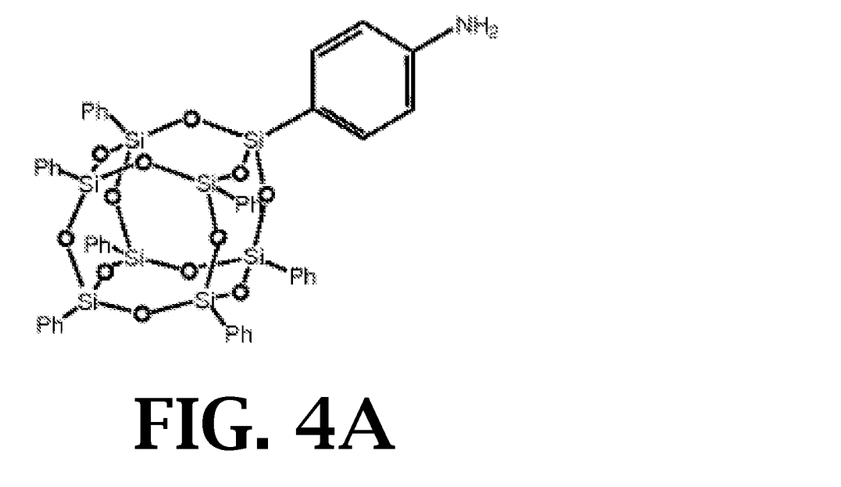
FIGS. 4A and 4B illustrate chemical structures of heptaphenyl-monoaniline-T8 POSS with amine functionality either in the para (FIG. 4A) or meta (FIG. 4B) position relative to phenyl group attachment to the Si atom.
Figure 4B:
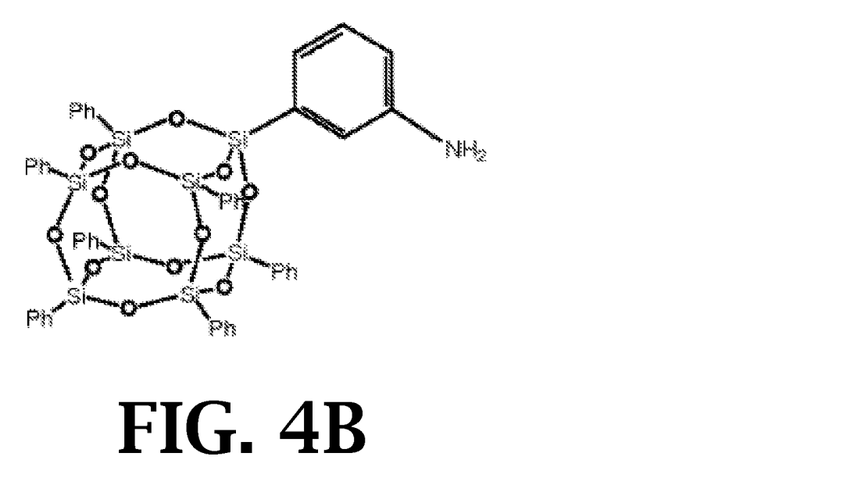
Figure 5:
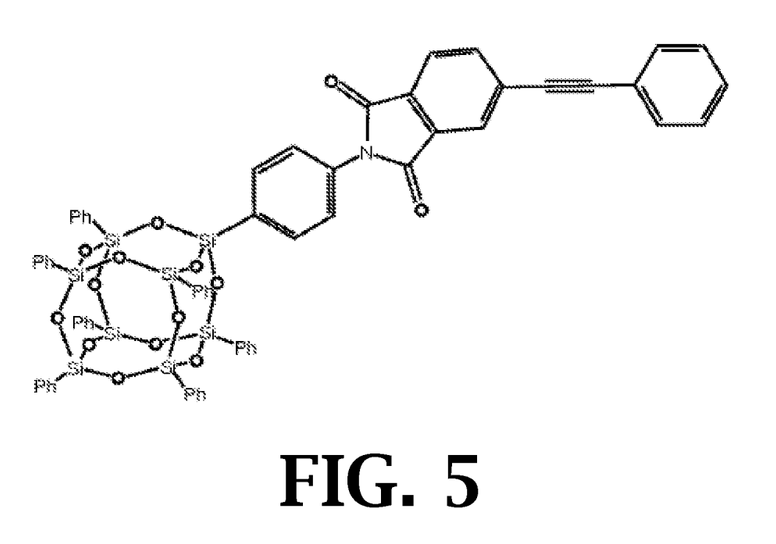
FIG. 5 illustrates the chemical structure for heptaphenyl-monoaniline-T8 POSS reacted with phenylethynyl phthalic anhydride ("PEPA") to form phenylethynyl phthalimide ("PEPI"), wherein the PEPI functionality can either be in the para or meta position relative to phenyl group attachment to the Si atom.
Figure 6:
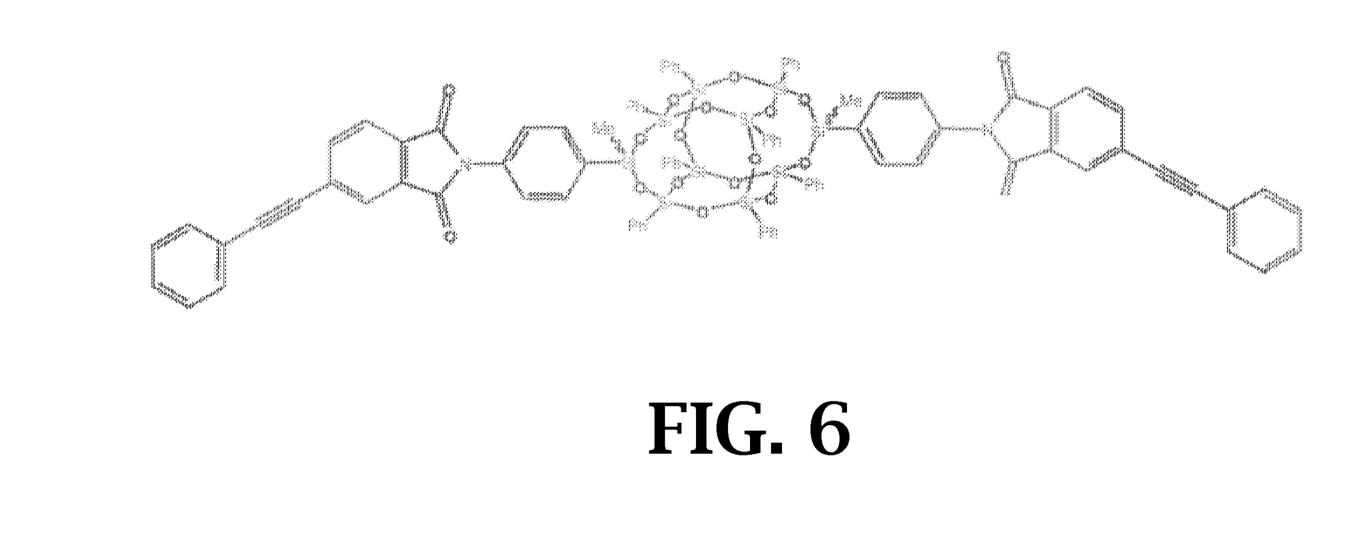
FIG. 6 is an example of the reaction product between a "bead-type" POSS isomer and PEPA.

Synthesis of bis(para-aniline,methyl)silyloxy-octaphenylsilsesquioxane: under a nitrogen atmosphere, in a 50 mL round-bottomed flask phenylPOSS-tetrol, Phenyl$_8$Si$_8$O$_{10}$(OH$_4$), (2.00 g, 1.87 mmol) was suspended in 10 mL of anhydrous THF. To this stirred suspension, a solution of 4-[bis(N,N-trimethylsilyl)phenylaminio]methyldichlorosilane (1.376 g, 3.93 mmol) and NEt$_3$ (0.776 g, 7.67 mmol) in THF (10 mL) was slowly added in a drop-wise manner. After 30 min, the solution was filtered to remove NEt$_3$HCl (974 mg, 7.08 mmol, 95% theoretical) and the solvent was removed under vacuum. Approximately 1 mL of diethylether was added to the product followed by 20 mL of MeOH to make a well-stirred suspension of white-colored intermediate. The trimethylsilyl groups were hydrolyzed by the addition of 1 drop of concentrated acetic acid and 1 hr of stirring. The product was isolated by filtration and dried under a nitrogen stream to give a white powder in 77% yield (1.922 g, 1.44 mmol). $^1$H NMR (CDCl$_3$, δ) 7.83-7.10 ppm (m, 44H), 6.60 ppm (m, 4H), 3.3 ppm (broad s, 4H, NH2), 0.11 ppm (s, 6H). $^{29}$Si NMR (CDCl$_3$) −29.7 ppm, −78.2 ppm, −79.1 ppm, −79.3 ppm, −79.4 ppm (reference spectrum in FIG. 1).

5. Application of POSS Monoaniline for the Purposes of Thermosetting Polymer Modification To modify a conventional epoxy resin/aminated hardener system with POSS monoaniline, a mixture of amines is employed to cure the epoxy adhesive. In the specific example of DER 331 epoxy, having an epoxide equivalent weight of 189, cured with 4-4'-dimanodiphenyl sulfone ("DDS") possessing an amine H equivalent weight of 64, modified with 5% POSS monoaniline to 95% DDS in the amine mixture:

$$\text{Amine H } eq.wt.POSS = \frac{544}{2} = 272$$

$$phr \text{ Amine} = \frac{272 \times 100}{189} \times 0.05$$

$$= \frac{64 \times 100}{189} \times 0.95$$

$$= 39.37$$

$$phr \text{ POSS monoaniline amine} = 7.2$$

$$phr \text{ DDS} = 32.2$$

To 100 g DER 331 epoxy, 39.37 g DDS and 7.2 g POSS monoaniline are added and are homogenized with or without the use of a common solvent. If solvent is used it is driven off by vacuum drying at elevated temperature. The resulting resin may be cured with or without the use of pressure using the appropriate cure protocol for DDS. Alternatively, the resin may be used as an application to continuous fibers, such as graphite, to produce a prepreg material for use in composite material fabrication.

6. Application of "Bead-Type" POSS Dianiline for the Modification of a Thermosetting Oligomer According to the molar equivalents and weights of monomers shown in Tables 1 and 2, respectively, 6-FDA monomer was added to an NMP solution of ODA and/or POSS in a dry nitrogen environment. After allowing the reaction to proceed for 60 min, an NMP solution of PEPA was then added to produce a total concentration of 10 wt % solids. The reaction was allowed to stir overnight in a dry nitrogen environment. 15 mL of toluene was added and the reaction was heated to 155° C. using the Dean-Stark methodology to promote imidization. FTIR is used to ensure the achievement of full imidization. A solvent extraction to separate NMP from oligomer was then performed using 15 mL of chloroform and distilled water. Excess chloroform was removed under reduced pressure; the reaction mixture was then added drop-wise to methanol and allowed to stir overnight. The solid product was collected by filtration and washed with methanol. The solid product was dried under vacuum and subsequently characterized by $^1$H, $^{13}$C, and $^{29}$Si NMR.

TABLE 1

Equivalents of monomers used to synthesize each of the oligoimides.

| | Compound | | | |
|---|---|---|---|---|
| | PEPA | 6-FDA | ODA | POSS |
| | | Mol. Wt. | | |
| | 248.23 | 444.24 | 200.24 | 1335.98 |
| Formula | $C_{16}H_8O_3$ | $C_{19}H_6F_6O_6$ | $C_{12}H_{12}N_2O$ | $C_{62}H_{58}N_2O_{14}Si_{10}$ |
| 0 POSS | 2 | 4 | 5 | 0 |
| 1 POSS | 2 | 4 | 4 | 1 |
| 2 POSS | 2 | 4 | 3 | 2 |
| 3 POSS | 2 | 4 | 2 | 3 |
| 4 POSS | 2 | 4 | 1 | 4 |
| 5 POSS | 2 | 4 | 0 | 5 |

TABLE 2

Amounts of monomers used in each of the six oligoimides.

| Target Oligomer (Avg. mol. for.) | Molecular Weight | mmoles in 7.00 g | PE (g) | 6-FDA (g) | ODA (g) | POSS (g) | Wt % $Si_{10}O_{14}$ |
|---|---|---|---|---|---|---|---|
| $C_{168}H_{80}F_{24}N_{10}O_{25}$ | 3094.45 | 2.2624 | 1.1228 | 4.0194 | 2.2645 | 0.000 | 0.00 |
| $C_{218}H_{126}F_{24}N_{10}O_{38}SiO_{10}$ | 4230.19 | 1.6548 | 0.8218 | 2.9407 | 1.3251 | 2.2106 | 8.33 |
| $C_{268}H_{172}F_{24}N_{10}O_{51}Si_{20}$ | 5365.94 | 1.3048 | 0.6475 | 2.3184 | 0.7840 | 3.4853 | 13.16 |
| $C_{318}H_{218}F_{24}N_{10}O_{64}Si_{30}$ | 6501.69 | 1.0766 | 0.5348 | 1.9131 | 0.2620 | 4.3148 | 16.31 |
| $C_{368}H_{264}F_{24}N_{10}O_{77}Si_{40}$ | 7637.44 | 0.9163 | 0.4550 | 2.3289 | 0.1834 | 4.8979 | 18.48 |
| $C_{418}H_{310}F_{24}N_{10}O_{90}Si_{50}$ | 8773.18 | 0.7980 | 0.3962 | 1.4175 | 0.0000 | 5.3298 | 20.16 |

7. Application of "Pendant-Type" PEPI POSS to the Modification of a Thermosetting Oligomer

To 10 g of a thermosetting oligomer powder comprised of repeat units consisting of the monomers 6-FDA and ODA, end-capped with PEPA, 10 wt %, or 1.11 g of "bead-type" PEPI POSS powder is added. The resultant binary powder mixture may be homogenized by (A) melt blending with conventional polymer blending and compounding equipment between the temperatures of 220° C. and 270° C. for 5 min followed by injection into an appropriately shaped mold and cured under a pressure of 100 psi at 371° C. for 1 hr or (B) dissolving the resultant binary powder mixture in a common solvent, such as NMP, at a solute concentration of 10 wt %, and precipitated with the use of a common non-solvent, such as methanol. The resultant powder is isolated and dried. The isolated material may be compression molded in purely resin form at 100 psi and cured in-situ, at 371° C. for 1 hr. Alternatively, the co-solution of the binary mixture may be used as an application to continuous fibers, such as graphite, and the majority of the solvent may be driven off using an oven, to produce a prepreg material for use in composite material fabrication.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of synthesizing a polyhedral oligomeric silsesquioxane, the method comprising:
   corner-capping an uncondensed polyhedral oligomeric silsesquioxane having an inorganic core comprising 6-14 silicon atoms, at least one of the silicon atoms being an M-type silicon atom or a D-type silicon atom, and at least one of the silicon atoms being a T-type silicon atom; and 9-20 oxygen atoms with an anhydride such that a phenyl moiety or an aniline is covalently coupled to at least one T-type silicon atom and a meta- or para-aniline group is covalently coupled to at least one D-type or M-type silicon atom.

2. The method of claim 1, wherein the polyhedral oligomeric silsesquioxane has a structure selected from:

and wherein the symbol Ph is representative of a phenyl moiety or an aniline moiety, the method comprising:
   corner-capping an uncondensed phenyl polyhedral oligomeric silsesquioxane with a halogenated trimethylsilyl amine.

3. A method of synthesizing a polyhedral oligomeric silsesquioxane having a structure:

the method comprising:

reacting the para-aniline polyhedral oligomeric silsesquioxane of claim 2 with phenylethynyl phthalic anhydride.

4. The method of claim 1, wherein the polyhedral oligomeric silsesquioxane has a structure:

wherein the symbol Ph is representative of a phenyl moiety or an aniline moiety and the symbol Me is representative of a methyl group, the method comprising:

reacting a phenylPOSS-tetrol with 3-[bis(N,N-trimethylsilyl)phenylamino]methyl-dichlorosilane; and hydrolyzing trimethysilyl groups.

5. The method of claim 1, wherein the polyhedral oligomeric silsesquioxane has a structure:

wherein the symbol Ph is representative of a phenyl moiety or an aniline moiety and the symbol Me is representative of a methyl group, the method comprising:

reacting a phenylPOSS-tetrol with 4-[bis(N,N-trimethylsilyl)phenylamino]methyl-dichlorosilane; and hydrolyzing trimethysilyl groups.

6. The method of claim 1, wherein the polyhedral oligomeric silsesquioxane has a structure:

wherein the symbol Ph is representative of a phenyl moiety or an aniline moiety and the symbol Me is representative of a methyl group, the method comprising:

reacting a phenylPOSS-tetrol with 4-[bis(N,N-trimethylsilyl)phenylamino]methyl-dichlorosilane and 3-[bis(N,N-trimethylsilyl)phenylamino]methyl-dichlorosilane; and hydrolyzing trimethysilyl groups.

7. The method of claim 1, wherein the polyhedral oligomeric silsesquioxane has a structure:

the method comprising:
reacting a cis- or trans-bis(para-aniline, methyl)silyoxy-octaphenylsilsesquioxane with phenylethynyl phthalic anhydride.

8. The method of claim 1, wherein the polyhedral oligomeric silsesquioxane has a structure selected from:

the method comprising:
reacting a pendant-type polyhedral oligomeric silsesquioxane having two para-aniline groups with phenylethynyl phthalic anhydride.

9. A method of synthesizing a thermosetting oligomeric imide, the method comprising:
reacting the meta- or para-aniline group of the polyhedral oligomeric silsesquioxane of claim 1 with monomers of a polymer host.

10. The method of claim 9, wherein the monomer is an anhydride and the polymer host is a polyimide, the monomer is a carboxylic acid and the polymer host is a polyamide, the monomer is an isocyanate and the polymer host is a polyurea, or the monomer includes a phenol and a formaldehyde and the polymer host is a benzoxazine.

11. The method of claim 9, the polymer host having a phenylethynyl functionality, the method further comprising:
melting the polyhedral oligomeric silsesquioxane of claim 9 with the polymer host; and
curing the melted polyhedral oligomeric silsesquioxane of claim 9 with the polymer host to form a crosslinked polymer network.

12. The method of claim 9, wherein the polymer host is an epoxy or a cyanate ester.

13. A method of synthesizing a polyhedral oligomeric silsesquioxane having a structure selected from:

wherein the symbol Ph is representative of a phenyl moiety or an aniline moiety, the method comprising:
corner-capping an uncondensed phenyl polyhedral oligomeric silsesquioxane with a halogenated trimethylsilyl amine; and
reacting the condensed phenyl polyhedral oligomeric silsesquioxane with phenylethynyl phthalic anhydride.

14. A method of synthesizing a polyhedral oligomeric silsesquioxane having a structure:

wherein the symbol Ph is representative of a phenyl moiety or an aniline moiety and the symbol Me is representative of a methyl group, the method comprising:
reacting a phenylPOSS-tetrol with 4-[bis(N,N-trimethylsilyl)phenylamino]methyl-dichlorosilane, 3-[bis(N,N-trimethylsilyl)phenylamino]methyl-dichlorosilane, or both; and
hydrolyzing trimethysilyl groups.

* * * * *